United States Patent [19]

Seki et al.

[11] 4,159,372

[45] Jun. 26, 1979

[54] PROCESS FOR PREPARING CEPHALOSPORIN ESTERS IN THE PRESENCE OF LIQUID SULFUR DIOXIDE

[75] Inventors: Shigeo Seki, Tokyo; Satoru Nakabayashi, Yokohama; Ken Nishihata, Yokohama; Nobuo Itoh, Yokohama; Toshinori Saito, Yokohama; Masahiro Onodera, Takatsuki; Shunzo Fukatsu, Tokyo, all of Japan

[73] Assignee: Meiji Seika Kaisha Ltd., Tokyo, Japan

[21] Appl. No.: 883,812

[22] Filed: Mar. 6, 1978

[30] Foreign Application Priority Data

Mar. 14, 1977 [JP] Japan .................................. 52-26950

[51] Int. Cl.$^2$ .......................................... C07D 501/04
[52] U.S. Cl. ......................................... 544/16; 544/26; 544/30
[58] Field of Search ............................... 544/30, 16, 26

[56] References Cited

U.S. PATENT DOCUMENTS

| 3,928,333 | 12/1975 | Wheeler | 424/246 |
| 4,115,646 | 9/1978 | Bently et al. | 544/26 |

OTHER PUBLICATIONS

Flynn, Ed., "Cephalosporins & Penicillins", (1972) pp. 147–151, 172–176.
Cocker et al., J. Chem. Soc., 1966, 1142.

*Primary Examiner*—Mark L. Berch
*Attorney, Agent, or Firm*—Frishauf, Holtz, Goodman & Woodward

[57] ABSTRACT

A process for preparing a cephalosporin ester which comprises subjecting an organic halide or an alcohol to reaction with a cephalosporin acid, a cephalosporin acid halide or a salt thereof in the presence of liquid sulfur dioxide.

6 Claims, No Drawings

PROCESS FOR PREPARING CEPHALOSPORIN ESTERS IN THE PRESENCE OF LIQUID SULFUR DIOXIDE

This invention relates to a process for preparing a cephalosporin ester. More particularly, this invention relates to a process for preparing a cephalosporin ester represented by formula (III)

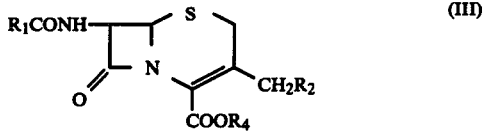

wherein $R_1CO$ represents an acyl group which may or may not have a protected or unprotected amino group; $R_2$ represents a hydrogen atom, an acyloxy group, a carbamoyloxy group or a group $-S-R_3$ (in which $R_3$ means an alkyl group having 1 or 2 carbon atoms or a heterocyclic group); and $R_4$ represents a lower-alkyl group having 1–4 carbon atoms, a halogen-containing lower-alkyl group having 1–4 carbon atoms, or a mono-, di- or tri-Y-substituted-phenylmethyl group (in which Y means a group selected from the class consisting of a hydrogen atom, a halogen atom, a methoxy group and a nitro group), or a mono-, di- or tri-Y-substituted-phenacyl group (in which Y has the same meaning as mentioned above), a straight-chain or branched acyloxymethyl group having 2–5 carbon atoms, or a mono-, di- or tri-Y-substituted-benzoyloxymethyl group (in which Y has the same meaning as mentioned above), which comprises subjecting a compound represented by formula (II)

wherein $R_4$ has the same meaning as mentioned above and $X_2$ represents a halogen atom or a hydroxyl group, to reaction with a compound represented by formula (I)

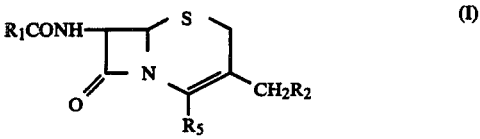

wherein $R_1CO$ and $R_2$ have the same meanings as mentioned above and $R_5$ represents a group

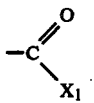

(in which $X_1$ means a hydroxyl group or a halogen atom) or a group

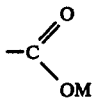

(in which M means a cation derived from an alkali metal, an alkyl amine or a heterocyclic amine), in the presence of liquid sulfur dioxide.

Namely, this invention relates to a process for the esterification of a compound represented by formula (I) with a compound represented by formula (II) at a low temperature in the presence of a base by using, as a solvent, liquid sulfur dioxide or a mixture of liquid sulfur dioxide and an inert solvent.

A lot of investigations have hitherto been carried out for developing a pharmaceutical for oral administration by the esterification of a β-lactam group antibiotic. It has been difficult to obtain a cephalosporin ester of high purity by a simple procedure, since a cephalosporin antibiotic easily undergoes a rearrangement of the double bond in the main nucleus from $\Delta^3$ to $\Delta^2$ in the presence of a base during the esterification reaction.

For instance, the sodium salt of cephalothin gives a mixture of the $\Delta^2$- and $\Delta^3$-forms of the acetoxymethyl ester by the reaction with chloromethyl acetate. As the methods for obtaining a pure $\Delta^3$-ester which is active orally, there have been reported a method in which an isomeric mixture is separated and purified by column chromatography; a method in which a mixture of the $\Delta^2$- and $\Delta^3$-forms is converted into a $\Delta^3$-sulfoxide by oxidation and then reduced to form a $\Delta^3$-cephalothin ester; a method in which the esterification is effected by adding a base over a long period of time so that the base may not be in excess amount no matter how temporally it may be (Eli Lilly and Company, Japanese Patent Provisional Publication No. Sho-51-16687/1976); and so on. In all methods, however, it is difficult to effect the esterification without isomerization from a $\Delta^3$-form to a $\Delta^2$-form. It is reported by Murphy et al in org. Chem., 35, 2429 (1970) that the isomerization from a $\Delta^3$-form to a $\Delta^2$-form is caused during reaction even in the esterification via a $\Delta^3$-cephalosporin acid chloride.

As a result of various investigations concerning the esterification of cephalosporin antibiotics, the present inventors found that, when the esterification mentioned above is carried out by using liquid sulfur dioxide or a mixed solvent containing liquid sulfur dioxide, a pure $\Delta^3$-cephalosporin ester can surprisingly be obtained in high yield without any rearrangement of the double bond even in the presence of a base and the esterification reaction proceeds fast to be completed in a short period of time even at a low reaction temperature (at a reflux temperature of liquid sulfur dioxide: in a range of $-15°$ to $0°$ C.). As the advantageous points of this invention, there may be mentioned that the solvent can readily be removed after reaction; that the reaction can be carried out at a low temperature; that liquid sulfur dioxide is not expensive industrially; and so on. Liquid sulfur dioxide which is important for industrial manufacture easily dissolves organic compounds and selectively solvates an anion. Further, it is considered that a $\Delta^2$-isomer is not by-produced and the esterification reaction proceeds readily because of the great ionizing power of liquid sulfur dioxide. The present invention can be utilized not only for an esterification reaction but also for other chemical modification conducted in the presence of a base, since the present invention utilizes the characteristics as a solvent of liquid sulfur dioxide.

For $R_1CO$ in formula (I) mentioned above, there may be exemplified the following groups:
2-thienylacetyl, phenylacetyl, phenoxyacetyl, 2-hydroxyphenylacetyl, 2-aminophenylacetyl, 2-amino-p-hydroxyphenylacetyl, 1-tetrazolylacetyl, 5-amino-5-carboxyvaleroyl, etc.

For —$R_3$ in —S—$R_3$ which is represented by $R_2$ in formula (I) there may be mentioned, as a heterocyclic group, a 5- or 6-membered cyclic group having 3 to 4 nitrogen, oxygen or sulfur atoms and exemplified a 1,3,4-thiadiazole group such as 1,3,4-thiadiazol-5-yl, 2-methyl-1,3,4-thiadiazol-4-yl, etc.; a tetrazole group such as 1-methyl-1,2,3,4-tetrazol-4-yl etc.; a 1,3,4- or 1,2,4-triazole group such as 1,3,4-triazol-5-yl, 3-carboxymethyl-1,2,4-triazol-5-yl, etc.; a 1,3,4-oxadiazole group; and so on.

For $R_4$ in formula (III), there may be exemplified the followings: a lower-alkyl group having 1–4 carbon atoms, e.g., methyl, ethyl, isopropyl, t-butyl, etc. and a substituted lower-alkyl group, the alkyl group per se having 1–4 carbon atoms, e.g., a chloromethyl group; a benzyl group; a mono-, di- or tri-substituted benzyl group, e.g., p-chlorobenzyl, p-methoxybenzyl, p-nitrobenzyl, 2,4-dinitrobenzyl, 2,4,6-trinitrobenzyl, 2,4-dinitro-6-methoxybenzyl, etc.; a phenacyl group; a mono-, di- or tri-substituted phenacyl group, e.g., p-chlorophenacyl, p-methoxyphenacyl, p-nitrophenacyl, 2,4-dinitrophenacyl, 2,4,6-trinitrophenacyl, 2,4-dinitro-6-methoxyphenacyl, acetoxyphenacyl, propionyloxyphenacyl, etc.; an acyloxymethyl group, e.g., isobutyryloxymethyl, pivaloyloxymethyl, etc.; and so on.

The esterification reaction of this invention will concretely be explained below.

The starting material represented by general formula (I) may be in the form of a free acid, an alkali metal salt thereof (or an alkylamine salt or a heterocyclic amine salt thereof) or an acid halide. As the alkali metal salt may be mentioned a salt of lithium, potassium, sodium or the like. As the alkylamine salt may be mentioned a salt of a tertiary amine salt such as trimethylamine, triethylamine, etc., and so on. As the heterocyclic amine salt may be mentioned a salt of pyridine, dimethylaminopyridine, imidazole, N-methylmorpholine or the like. As the acid halide may be exemplified preferably an acid chloride, an acid bromide or the like. In cases where a free acid or a salt thereof is used as the starting material, one of them is dissolved or suspended in liquid sulfur dioxide or in a mixture of liquid sulfur dioxide and an inert solvent. In the case of a free acid, after it is converted into a salt of an organic base by adding 1.0–2.0 equivalents, preferably 1.0–1.2 equivalents of an organic base, preferably a tertiary amine such as pyridine, triethylamine, etc., 1– 3 equivalents of an organic halogen compound represented by general formula (II) is added thereto and then the mixture is refluxed for 1–10 hours at a boiling temperature of liquid sulfur dioxide or a mixed solvent containing the same to complete the reaction. The preferable reaction temperature ranges from −15° to −5° C. As the inert solvent to be used for a mixed solvent may be mentioned for example methylene chloride, chloroform, carbon tetrachloride, tetrahydrofuran, dioxane, ethylene glycol dimethyl ether, diethylene glycol dimethyl ether, etc. The ratio of the inert solvent to the liquid sulfur dioxide to be mixed with each other is optional if only a base and liquid sulfur dioxide to be added or existing in the reaction system are present each in an amount of not less than one equivalent against the starting compound to be esterified. The preferable amount of liquid sulfur dioxide to be used is in the range of 15–30 times by weight of the starting compound. In cases where an acid chloride is used as the starting material, an alcohol represented by general formula (II) is dissolved, together with a base, preferably pyridine, in the inert solvent mentioned above and liquid sulfur dioxide is added thereto. Next, after an acid halide represented by general formula (I) is added thereto, the mixture is refluxed for 1–8 hours to complete the reaction. As the acid halide to be used for the purpose, there may be exemplified an acid chloride, an acid bromide or the like. The amount of liquid sulfur dioxide to be used is similar to that in the case of a free acid.

After reaction, the solvent is removed by distillation and the residue is dissolved in a suitable solvent. The solution is washed with water, a diluted hydrochloric acid, a diluted aqueous sodium hydrogen carbonate and a saturated aqueous sodium chloride. The organic layer is concentrated, after dried, to afford a $\Delta^3$-cephalosporin ester (III). Further, the product is recrystallized, if necessary, from a suitable solvent to give a $\Delta^3$-cephalosphorin ester (III) of high purity.

The present invention will be explained more detailedly by the following Examples, which, however, should not be construed to limit the present invention.

EXAMPLE 1 t-Butyl 7-(2-thienylacetamido)cephalosporanate

Into a 100 ml. four-necked flask placed on a magnetic stirrer and equipped with a reflux condenser for cooling low-boiling substances, a thermometer and a gas inlet tube were introduced a stirrer and 1.98 g. (5 mmol.) of 7-(2-thienylacetamido)cephalosporanic acid. After the reflux condenser for cooling low-boiling substances was cooled by using methanol and dry-ice, sulfur dioxide gas was introduced from a bomb through the gas inlet tube into the flask and liquified after cooled in the reflux condenser. When about 10 ml. of liquid sulfur dioxide was introduced, the bomb was closed and then 0.6 g. (6 mmol.) of triethylamine was added with care.

Next, after 3.4 g. (25 mmol.) of 6-butyl bromide was added, the mixture was refluxed for 4 hours. After reaction, the liquid sulfur dioxide was distilled out to give an oily substance. The thus obtained substance was dissolved in 100 ml. of methylene chloride and washed successively with 20 ml. of water, 50 ml. of a diluted hydrochloric acid, 50 ml. of a saturated aqueous sodium hydrogen carbonate and 30 ml. of a saturated aqueous sodium chloride. After the organic layer was dried over anhydrous magnesium sulfate, it was concentrated. The residue was recrystallized from a mixture of ethyl acetate and isopropyl ether to give 0.9 g. of t-butyl 7-(2-thienylacetamido)cephalosporanate as a crystal. NMR spectrum of the product did not show the existence of the $\Delta^2$-form. Yield: 40%. Melting point: 138°–140° C.

EXAMPLE 2

Benzhydryl 7-(2-thienylacetamido)cephalosporanate

According to the same procedure as in Example 1, 1.98 g. (5 mmol.) of 7-(2-thienylacetamido)cephalosporanic acid, 1.5 g. (7.4 mmol.) of α-chlorodiphenylmethane and 0.49 ml. of pyridine were subjected to reaction in about 10 ml. of liquid sulfur dioxide for 3.5 hours. The reaction mixture was treated as in Example 1 and then recrystallized from a mixture of ethyl acetate and ether to give 2.5 g. of benzhydryl 7-(2-thienylacetamido)cephalosporanate as a crystal. Yield: 89%. Melting point: 142°–143° C.

EXAMPLE 3 p-Methoxybenzyl 7-(2-thienylacetamido)cephalosporanate

According to the same procedure as in Example 1, 0.792 g. (2 mmol.) of 7-(2-thienylacetamido)cephalosporanic acid, 0.625 g. (4 mmol.) of p-methoxybenzyl chloride and 0.4 g. (4 mmol.) of triethylamine were subjected to reaction in 10 ml. of liquid sulfur dioxide for 4 hours. After recrystallization from a mixture of ethyl acetate and ether, 0.6 g. of p-methoxybenzyl 7-(2-thienylacetamido)cephalosporanate was obtained as a crystal. NMR spectrum of the product did not show the existence of the $\Delta^2$-form. Yield: 59%. Melting point: 150°–151° C.

EXAMPLE 4

Phenacyl 7-(2-thienylacetamido)cephalosporanate

According to the same procedure as in Example 1, 0.792 g. (2 mmol.) of 7-(2-thienylacetamido)cephalosporanic acid, 0.796 g. (4 mmol.) of phenacyl bromide and 0.4 g. (4 mmol.) of triethylamine were subjected to reaction in 10 ml. of liquid sulfur dioxide for 4 hours. After recrystallization from a mixture of ethyl acetate and ether, 0.76 g. of phenacyl 7-(2-thienylacetamido)cephalosporanate was obtained as a crystal. NMR spectrum of the product did not show the existence of the $\Delta^2$-form. Yield: 74%. Melting point: 177°–177.5° C.

EXAMPLE 5

Phenacyl 7-(phenoxyacetamido)cephalosporanate

According to the same procedure as in Example 1, 0.696 g. (2 mmol.) of 7-(phenoxyacetamido)deacetoxycephalosporanic acid, 0.796 g. (4 mmol.) of phenacyl bromide and 0.4 g. of triethylamine were subjected to reaction in 10 ml. of liquid sulfur dioxide for 4 hours. The reaction mixture was treated as in Example 1 and then recrystallized from a mixture of ethyl acetate and ether to give 0.76 g. of phenacyl 7-(phenoxyacetamido)deacetoxycephalosporanate as a crystal. NMR spectrum of the product did not show the existence of the $\Delta^2$-form. Yield: 82%. Melting point: 170.5°–171.5° C.

EXAMPLE 6

Acetoxymethyl 7-(2-thienylacetamido)cephalosporanate

According to the same procedure as in Example 1, 0.99 g. (2.5 mmol.) of 7-(2-thienylacetamido)cephalosporanic acid, 0.8 g. (4 mmol.) of acetoxymethyl iodide and 0.31 g. (3 mmol.) of triethylamine were subjected to reaction in 10 ml. of liquid sulfur dioxide for 8 hours. After recrystallization from a mixture of methylene chloride and isopropyl ether, 0.97 g. of acetoxymethyl 7-(2-thienylacetamido)cephalosporanate was obtained as a crystal. NMR spectrum of the product did not show the existence of the $\Delta^2$-form. Yield: 83%. Melting point: 144°–145° C.

EXAMPLE 7

Acetoxymethyl 7-(2-thienylacetamido)cephalosporanate

According to the same procedure as in Example 1, 0.99 g. (2.5 mmol.) of 7-(2-thienylacetamido)cephalosporanic acid, 0.61 g. (4 mmol.) of acetoxymethyl bromide and 0.31 g. (3 mmol.) of triethylamine were subjected to reaction in 10 ml. of liquid sulfur dioxide for 8 hours. After recrystallization from a mixture of methylene chloride and isopropyl ether, 0.7 g. of acetoxymethyl 7-(2-thienylacetamido)cephalosporanate was obtained as a crystal. NMR spectrum of the product did not show the existence of the $\Delta^2$-form. Yield: 60%. Melting point: 144°–145° C.

EXAMPLE 8

Acetoxymethyl 7-(phenylacetamido)deacetoxycephalosporanate

According to the same procedure as in Example 1, 0.66 g. (2 mmol.) of 7-(phenylacetamido)cephalosporanic acid, 0.8 g. (4 mmol.) of acetoxymethyl iodide and 0.31 g. (3 mmol.) of triethylamine were subjected to reaction in 10 ml. of liquid sulfur dioxide for 8 hours. After recrystallized from a mixture of methylene chloride and isopropyl ether, 0.62 g. of acetoxymethyl 7-(phenylacetamido)deacetoxycephalosporanate was obtained as a crystal. NMR spectrum of the product did not show the existence of the $\Delta^2$-form. Yield: 76.5%. Melting point: 134°–135° C.

EXAMPLE 9

Pivaloyloxymethyl 7-(2-thienylacetamido)cephalosporanate

According to the same procedure as in Example 1, 0.99 g. (2.5 mmol.) of 7-(2-thienylacetamido)cephalosporanic acid, 0.97 g. (4 mmol.) of pivaloyloxymethyl iodide and 0.42 g. (4 mmol.) of triethylamine were subjected to reaction in 10 ml. of liquid sulfur dioxide for 8 hours. After recrystallization from a mixture of methylene chloride and isopropyl ether, 0.67 g. of pivaloyloxymethyl 7-(2-thienylacetamido)cephalosporanate was obtained as a crystal. NMR spectrum of the product did not show the existence of the $\Delta^2$-form. Yield: 52%. Melting point: 69°–71° C.

EXAMPLE 10

Benzoyloxymethyl 7-(2-thienylacetamido)cephalosporanate

According to the same procedure as in Example 1, 0.99 g. (2.5 mmol.) of 7-(2-thienylacetamido)cephalosporanic acid, 1.0 g. (4 mmol.) of benzoyloxymethyl iodide and 0.42 g. (4 mmol.) of triethylamine were subjected to reaction in 10 ml. of liquid sulfur dioxide for 8 hours. After recrystallization from a mixture of methylene chloride and isopropyl ether, 0.24 g. of benzoyloxymethyl 7-(2-thienylacetamido)cephalosporanate was obtained as a crystal. NMR spectrum of the product did not show the existence of the $\Delta^2$-form. Yield: 18%. Melting point: 181°–182.5° C.

EXAMPLE 11

Trityl 7-(phenoxyacetamido)deacetoxycephalosporanate

In a mixture of 30 ml. of liquid sulfur dioxide and 20 ml. of chloroform were dissolved 3.5 g. (10.1 mmol.) of 7-(phenoxyacetamido)deacetoxycephalosporanic acid and 4.2 g. (15.1 mmol.) of trityl chloride. Under gentle refluxing of the liquid sulfur dioxide, 2 ml. of pyridine was gradually added dropwise. After 2 hours of reaction, the solvent was removed by evaporation to obtain an oily substance.

The thus obtained oily substance was dissolved in chloroform and washed with an acidic water. The oily substance was further washed with a saturated aqueous sodium hydrogen carbonate and with a saturated aqueous sodium chloride followed by the distillation under reduced pressure of the solvent to concentrate the solution. Then, the concentrate was diluted with ether to give 4.0 g. of the desired trityl ester as a crystal. A single spot was observed on the thin layer chromatogram (TLC) of the product. Nuclear magnetic resonance spectrum (NMR) of the product showed only the $\Delta^3$-form. Yield: 67.4%. Melting point: 182° C.

EXAMPLE 12 p-Nitrobenzyl 7-(2-thienylacetamido)cephalosporanate

In a mixture of 5 ml. of chloroform and 5 ml. of liquid sulfur dioxide was dissolved 396 mg. (1.2 mmol.) of 7-(2-thienylacetamido)cephalosporanic acid. While the liquid sulfur dioxide was refluxed gently, 0.21 ml. of triethylamine was added dropwise thereinto. After completion of the dropwise addition thereof, 324 mg. (1.5 mmol.) of p-nitrobenzylbromide was added and the mixture was refluxed for 3.5 hours. After removal of the solvent by distillation under reduced pressure, the oily substance obtained was dissolved in ethyl acetate and washed with water under acidic conditions. The organic layer was further washed with a saturated aqueous sodium hydrogen carbonate and then with a saturated aqueous sodium chloride. After the organic layer was dried over anhydrous magnesium sulfate, the ethyl acetate was removed by distillation under reduced pressure. To the concentrate was added ether to obtain 224 mg. of the desired p-nitrobenzyl ester as a crystal. NMR spectrum of the product did not show the existence of the $\Delta^2$-form. Yield: 42%. Melting point: 154°–156° C.

EXAMPLE 13 p-Nitrobenzyl 7-(2-thienylacetamido)cephalosporanate

In 2 ml. of methylene chloride were dissolved 153 mg. (1 mmol.) of p-nitrobenzyl alcohol and 80 mg. (1 mmol.) of pyridine and then 2 ml. of liquid sulfur dioxide was condensed thereinto. Next, 210 mg. (0.5 mmol.) of 7-(2-thienylacetamido)cephalosporanic acid chloride was added thereto and the mixture was refluxed gently at 0° C. After 2 hours, the liquid sulfur dioxide and the methylene chloride were removed by distillation under reduced pressure. The residue was dissolved in ethyl acetate, and washed with 2% hydrochloric acid and with 5% aqueous sodium hydrogen carbonate. After the organic layer was dried, the solvent was removed by distillation under reduced pressure to afford an oily substance. The thus obtained substance was solidified with ether to give 176 mg. (66%) of the p-nitrobenzyl ester of 7-(2-thienylacetamido)cephalosporanic acid. The product showed a single spot on its thin layer chromatogram. Nuclear magnetic resonance spectrum of the product showed only the existence of the $\Delta^3$-form. Melting point: 154°–156° C.

EXAMPLE 14 p-Methoxybenzyl 7-(2-thienylacetamido)cephalosporanate

By using 140 mg. (1 mmol.) of anise alcohol, 100 mg. (1.25 mmol.) of pyridine, 3 ml. of methylene chloride, 3 ml. of liquid sulfur dioxide and 210 mg. (0.5 mmol.) of 7-(2-thienylacetamido)cephalosporanic acid chloride, the treatments were carried out in the same manner as in Example 13 to give 110 mg. (49%) of the desired p-methoxybenzyl ester. NMR spectrum of the product did not show the existence of the $\Delta^2$-form. Melting point: 150°–151° C.

EXAMPLE 15

2,2,2-Trichloroethyl 7-(2-thienylacetamido)cephalosporanate

By using 0.6 g. (4 mmol.) of 2,2,2-trichloroethanol, 0.32 g. (4 mmol.) of pyridine, 8 ml. of methylene chloride, 8 ml. of liquid sulfur dioxide and 0.84 g. (2 mmol.) of 7-(2-thienylacetamido)cephalosporanic acid chloride, the treatments were carried out in the same manner as in Example 13 to give 710 mg. (67%) of the 2,2,2-trichloroethyl ester. NMR spectrum of the product did not show the existence of the $\Delta^2$-form. Melting point: 119.5°–120.5° C.

EXAMPLE 16

Phenacyl 7-(2-thienylacetamido)cephalosporanate

By using 136 mg. (1 mmol.) of phenacyl alcohol, 80 mg. (1 mmol.) of pyridine, 2 ml. of methylene chloride, 3 ml. of liquid sulfur dioxide and 210 mg. (0.5 mmol.) of 7-(2-thienylacetamido)cephalosporanic acid chloride, the treatments were carried out in the same manner as in Example 13 to give 54 mg. (55%) of the phenacyl ester. NMR spectrum of the product did not show the existence of $\Delta^2$-form. Melting point: 177°–177.5° C.

What is claimed is:

1. A process for preparing a cephalosporin ester represented by the formula:

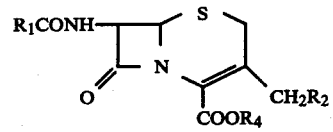

wherein $R_1CO$ represents an acyl group which may or may not have a protected or unprotected amino group; $R_2$ represents a hydrogen atom, an acetyloxy group, a carbamoyloxy group or a group —S—$R_3$ (wherein $R_3$ is an alkyl group having 1 or 2 carbon atoms or a heterocyclic group selected from the class consisting of a 1,3,4-thiadiazole group, a tetrazole group, a 1,3,4-triazole group, a 1,2,4-triazole group and a 1,3,4-oxadiazole group); and $R_4$ represents a lower-alkyl group having 1–4 carbon atoms, or a mono-, di- or tri-Y-substituted-phenylmethyl group (wherein Y is a group selected from the class consisting of a hydrogen atom, a halogen atom, a methoxy group and a nitro group), or a mono-, di- or tri-Y-substituted-phenyacyl group, a straight-chain or branched acyloxymethyl group having 2–5 carbon atoms, or a mono-, di- or tri-Y-substituted-benzoyloxymethyl group, which comprises subjecting a compound represented by the formula:

$R_4X_2$ wherein $R_4$ has the same meaning as mentioned above and $X_2$ represents a halogen atom or a hydroxyl group, to reaction with a compound represented by the formula:

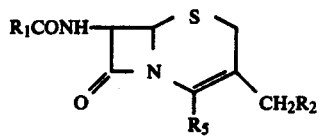

wherein $R_1CO$ and $R_2$ have the same meanings as mentioned above and $R_5$ represents a group

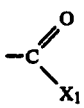

(wherein $X_1$ is a hydroxyl group or a halogen atom) or a group $$-C\begin{matrix}\nearrow O \\ \searrow OM\end{matrix}$$

(wherein M is a cation derived from an alkali metal, an alkylamine or a heterocyclic amine), in the presence of liquid sulfur dioxide.

2. A process as claimed in claim 1 wherein the reaction is conducted in liquid sulfur dioxide or a mixture of liquid sulfur dioxide and an inert solvent.

3. A process as claimed in claim 1 wherein the reaction is conducted at a temperature of $-15°$ to $-5°$ C.

4. A process as claimed in claim 1 wherein the reaction is conducted in the presence of a base in cases where $R_5$ represents a carboxyl group.

5. A process as claimed in claim 1 wherein the liquid sulfur dioxide is present in an amount of not less than one equivalent of the starting compound to be esterified.

6. A process as claimed in claim 5 wherein the liquid sulfur dioxide is present in an amount of 15–30 times by weight of the starting compound to be esterified.

* * * * *